(12) United States Patent
Meijer et al.

(10) Patent No.: US 9,890,432 B2
(45) Date of Patent: Feb. 13, 2018

(54) PRDM14 AND FAM19A4, MOLECULAR DIAGNOSTIC MARKERS FOR HPV-INDUCED INVASIVE CANCERS AND THEIR HIGH-GRADE PRECURSOR LESIONS

(71) Applicant: SELF-SCREEN B.V., Amsterdam (NL)

(72) Inventors: Christophorus Joannes Lambertus Maria Meijer, Amsterdam (NL); Petrus Josephus Ferdinandus Snijders, Amsterdam (NL); Renske Daniëla Maria Steenbergen, Amsterdam (NL)

(73) Assignee: SELF-SCREEN B.V., Amsterdam (NL)

( * ) Notice: Subject to any disclaimer, the term of this patent is extended or adjusted under 35 U.S.C. 154(b) by 96 days.

(21) Appl. No.: 14/434,866

(22) PCT Filed: Oct. 14, 2013

(86) PCT No.: PCT/NL2013/050729
§ 371 (c)(1),
(2) Date: Apr. 10, 2015

(87) PCT Pub. No.: WO2014/058321
PCT Pub. Date: Apr. 17, 2014

(65) Prior Publication Data
US 2015/0284815 A1 Oct. 8, 2015

(51) Int. Cl.
*C12Q 1/68* (2006.01)
*C07H 21/04* (2006.01)
*C12Q 1/70* (2006.01)

(52) U.S. Cl.
CPC .......... *C12Q 1/708* (2013.01); *C12Q 1/6886* (2013.01); *C12Q 2600/154* (2013.01)

(58) Field of Classification Search
None
See application file for complete search history.

(56) References Cited

U.S. PATENT DOCUMENTS

2013/0129668 A1* 5/2013 Firestein .............. C12Q 1/6883
424/85.1

FOREIGN PATENT DOCUMENTS

WO 2009128714 A1 10/2009

OTHER PUBLICATIONS

Teschendorff et al. (Genome Medicine, vol. 4, No. 24, pp. 1-14, Mar. 27, 2012).*
Wilting et al. (Molecular Cancer, vol. 9, No. 167, 2010).*
Teschendorff, Andrew E., et al.: "Epigenetic variability in cells of normal cytology is associated with the risk of future morphological transformation." Genome Medicine, vol. 4, No. 3, Mar. 24, 2012, pp. 1-14. XP-002694213.
Ying, Jianming, et al.: "Integrative cancer genomic and epigenectic analyses identity critical novel tumor suppressor genes at 3p14-12 for nasopharyngeal carcinoma." Proceedings of American Association of Cancer Research, vol. 47, 2006. XP-002694214.
Moelans, Cathy B., et al.: "Molecular profiling of invasive breast cancer by mulitplex ligation-dependent probe amplification-based copy number analysis of tumor suppressor and oncogenes." Modern Pathology: An Official Journal of The United States and Canadian Academy of Pathology, Inc., vol. 23, No. 7, Jul. 2010, pp. 1029-1039, XP-002694215.
Hu, Min, et al.: "Distinct epigenetic changes in the stromal cells of breast cancers." Nature Genetics, vol. 37, No. 8, Aug. 1, 2005, pp. 899-905. XP008124589.
Henken, FE, et al.: "Sequential gene promoter methylation during HPV-induced cervical carcinogenesis." British Journal of Cancer, Harcourt Publishers, vol. 97, No. 10, Nov. 19, 2007, pp. 1457-1464. XP009120044.
Wilting, Saskia M., et al.: "Methylation-mediated silencing and tumor suppressive function of hsa-miR-124 in cervical cancer." Molecular Cancer, Biomed Central, London, GB, vol. 9, No. 1, Jun. 26, 2010, pp. 167. XP021077905.

* cited by examiner

*Primary Examiner* — Jeanine A Goldberg
(74) *Attorney, Agent, or Firm* — Gianna Julian-Arnold; Saul Ewing Arnstein & Lehr LLP

(57) ABSTRACT

The invention relates to method for detecting HPV-induced high-grade precancerous lesions and HPV-induced invasive cancers, said method comprising detection of hypermethylation in the PRDM14 and/or FAM19A4 gene in a cell whereby such hypermethylation indicates the presence of HPV-induced precursor lesions with invasive potential and HPV-induced invasive cancers. The invention further comprises the use of the PRDM14 and/or FAM19A4 gene in such a method and a testkit for the detection of PRDM14 and/or FAM19A4 methylation.

6 Claims, 8 Drawing Sheets

Figure 1A: PRDM14 promoter, coding sequence, CpG rich sequence of intron 1 and 3'UTR

>hg19_knownGene_uc003xym.3 range=chr8:70963886-70984562 5'pad=0 3'pad=0
strand=- repeatMasking=none
cccgccagctttagggactctggcggcgtctcttagccgggtagatgttc
ctccttccctctctcttccaagccgctgccaggccggggtgaggctgc
acctcagtcttcagcccgaaggccgcgcccggggcggtcgctccccat
tcagctaagaggaagcagcggccggggggcaggcgaggaacctgtcccgg
ctcacccggcaagactgcgtttccccacctcggcgcttctttctgtga
atgtgaatggaactaagcgttcctttctctccctcaatggccggcgagga
gaattcaaatgcggtctttgggcgctcggtatgggtctggaccttggttt
tcagagcctgcgcgtccaaggtcgctagcctttcccgaaggaagtgacag
ctgcggcggcgcgggaggcccatcctcggtcgtttaaagccacttaagga
ataaaagccccgagagagcaaaacgaccacccgaaacctcggaagcgtc
gggggtgccgggcccaacgctcccacgtgtcactgccggggactcgcgag
gcgaagcttcccagcgctcaaggcgctcccgcctcgtccccaggtatcag
gaacagacacccaccaggtccaccagcgggtcagacgccgccttcgggca
ggctgggatcttccgaactggggagcggagagtaagggctcgaccccggg
acgcgagtccggccttctggactccggttcagggtgtgtgtgcgcgcgga
gggcttatctggggcgcctgggtagcacacgtgttcggttttttttctcc
ccgactccgcacgcctggagcggcaatactgcctgccctagaaggccagc
ggcgagtgctcgccactagggtcccagggagggtttggaaaactgatgag
ttaagtgagcgacccaggggacagagggcgagtcgagagtcggccaatg
gctgcggtgggcgggagaagacgacgcgggatctgcgtgggccgggtc
AATTCCCTACCCTCGACCTGTCGATGCCCCGCGGCCCCGCCCGCCCTCTT
AAGCCTGGCTCAGCCCTCAGGGCCCGCCCGAAGTCTACCGAGCCCGAGTG
GCCTACCGAGCCCGAGTGGCCCCGCAGCGTCCAGGAGGCGCCCGCTCCGC
GGTGGCGCTCTTGGAGGTGGTGTCGGAGgtaggcacgggacaggacgcgc
ctggggcccggggcggtggtcttccagggccgttggggagggcggcagca
ctcgctggcgcagttcgttttggatggtcgttctgccctctcgggggctt
tgaatcccaagttgcagatccctgaggtcggaggaggctaggagaagggc
gcctttggaggatcgggaggagacgggccgctgcctgtgtcgtggctgac
ctcttctcctgacccgtgttctttaatttctgagtcatgaccctgcttg
gttttcttattgggctcattgatctcaagacccgccggccctgaagggc
ttcattcttcagcctcggtgaacttgctgcctgtctattaaaacgccatc
ctttcccggcggtgcggggcgggaggactggcagtcgccgaggctcttc
gctcccacctggccaggctcgtccacgcggctcccgagggctaccccca
ggccccaatagtcctggtagaatgattggagtttccgaggaacccgggga
atgtggcggacgctgcccgcgagggaaaagaggttcaggcggcgcatcct
agggcagccaaaagtggcgcgccctccctgcgggcagtcaggaccgcc
aggacccgcggggtcacaccgctgggccagagcaggtcgcggggtccctg
gacctgcccggggctctgggagcgcgtctccatctgcgcggtgcgaccc
agggtcctcggctcttcctcccagccgagggccaggagcgcctggagc
tgtcgcttgctccattgccctccgaccgcctgcgctggctcccggccca
gcccgaggttggcagggcccgcggctcccacagacctaccaacgagt
tttgtaggactgagaagaaggaaggaaagggaacttcaatgggttttgca
ggaaccgggttgggggccgaaagcggagagcgggtgtgggaaggcggccg
ggcttagggaaggggtgcttggagagggaagggaaggcaacactaaccc
ggaatttagagtagggcaggatcccggcagatttccgtttggggcttttt
tgtgtttgcttctattgctgttttttcgttttgtcttaattgtgggagcg
ggctggcgggatcggactggggcgtttatcctgttcccttggatctggg
gctggctggggtggaggaggctggtggggaggcgcgggtcggacccggg

Figure 1B:

```
aagctcccgcgcggtgtcctcagcggcgcccgcttttctgcag.......
intron 1.......exon2-14: AGCCGCCGAGCGTGCGGTCCCG
GGATGGCTCTACCCCGGCCAAGTGAGGCCGTGCCTCAGGACAAGGTGTGC
TACCCGCCGGAGAGCAGCCCGCAGAACCTGGCCGCGTACTACACGCCTTT
CCCGTCCTATGGACACTACAGAAACAGCCTGGCCACCGTGGAGGAAGACT
TCCAACCTTTCCGGCAGCTGGAGGCCGCAGCGTCTGCTGCCCCGCCATG
CCCCCCTTCCCCTTCCGGATGGCGCCTCCCTTGCTGAGCCCGGGTCTGGG
CCTACAGAGGGAGCCTCTCTACGATCTGCCCTGGTACAGCAAGCTGCCAC
CGTGGTACCCAATTCCCCACGTCCCCAGGGAAGTGCCGCCCTTCCTGAGC
AGCAGCCACGAGTACGCGGGTGCCAGCAGTGAAGATCTGGGCCACCAAAT
CATTGGTGGCGACAACGAGAGTGGCCCGTGTTGTGGACCTGACACTTTAA
TTCCACCGCCCCTGCGGATGCTTCTCTGTTACCTGAGGGGCTGAGGACC
TCCCAGTTATTACCTTGCTCACCCAGCAAGCAGTCAGAGGATGGTCCCAA
ACCCTCCAACCAAGAAGGGAAGTCCCCTGCTCGGTTCCAGTTCACGGAGG
AGGACCTGCACTTCGTTCTGTACGGGGTCACTCCCAGCCTGGAGCACCCA
GCCAGCCTGCACCATGCGATTTCAGGCCTCCTGGTCCCCCCAGACAGCTC
TGGATCTGATTCTCTTCCTCAAACTCTGGATAAAGACTCCCTTCAACTTC
CAGAAGGTCTATGCCTCATGCAGACGGTGTTTGGTGAAGTCCCACATTTT
GGTGTGTTCTGCAGTAGTTTTATCGCCAAAGGAGTCAGGTTTGGGCCCTT
TCAAGGTAAAGTGGTCAATGCCAGTGAAGTGAAGACCTACGGAGACAATT
CTGTGATGTGGGAGATCTTTGAAGATGGTCATTTGAGCCACTTTATAGAT
GGAAAAGGAGGTACGGGGAACTGGATGTCCTATGTCAACTGTGCCCGCTT
CCCCAAGGAGCAGAACCTAGTTGCTGTGCAGTGTCAAGGGCATATATTTT
ATGAGAGCTGCAAAGAGATCCATCAGAACCAAGAGCTCCTTGTGTGGTAT
GGAGACTGCTATGAGAAATTTCTGGATATTCCTGTGAGCCTTCAGGTCAC
AGAGCCGGGGAAGCAGCCATCTGGGCCCTCTGAAGAGTCTGCAGAAGGCT
ACAGATGTGAAAGATGTGGGAAGGTATTTACCTACAAATATTACAGAGAT
AAGCACCTCAAGTACACCCCTGTGTGGACAAGGGCGATAGGAAATTTCC
CTGTTCTCTCTGCAAACGATCCTTTGAGAAGCGGGACCGGCTTCGGATCC
ACATTCTTCATGTTCATGAGAAGCACCGGCCTCACAAGTGTTCTACATGT
GGGAAATGTTTCTCTCAATCTTCCAGCCTAAACAAACACATGCGAGTCCA
CTCTGGAGACAGACCATACCAGTGTGTGTATTGTACTAAGAGGTTCACAG
CCTCCAGCATACTCCGCACACACATCAGGCAGCACTCCGGGGAGAAGCCC
TTCAAATGCAAGTACTGTGGTAAATCTTTTGCATCCCATGCTGCCCATGA
CAGCCATGTCCGGCGTTCACACAAGGAGGATGATGGCTGCTCATGCAGCA
TCTGTGGGAAAATCTTCTCAGATCAAGAAACATTCTACTCCCACATGAAG
TTTCATGAAGACTACTAGCCCTGCCAGGCACAATGACTCACGCCTGTAAT
CCCAGCACTTTGGGAGGCAGAGGTGGGTGGATCACTCAAGTCCAGGAGTT
CGAGACCAGCCTGGGCAACATGGTGAAATCCTGTCTCTACCAAAAAAATA
CAAAAATCAGCTGGGGGTGGTGGCACATGCCTGTGGTTCCAGCCACTCAG
GAGGTCGAGGTGGCAGGATGGTTTGAGCACAGGAGACGGAGGTTGCTGTG
AGCTGAGATCGCCCCACTGCTTTTCAACCTGGGTGACAGAACCAGACCCT
GTCTCAAAACAAAACAAAACAAAAAAATGAGTAGCCCTCAAGAGTGTGG
AGACAATGTAAAAACAAGAGATTCGGATTCTCTATTTCCTTTTATGGG
TTATAGAAGTCCCTGCAGTTGGCTGTGTGTGGTGGCTCACGCCT
```

Figure 2A: FAM19A4 promoter, coding sequence, CpG rich sequence of part of intron 1 and 3'UTR

>hg19_refGene_NM_001005527 range=chr3:68780915-68982761 5'pad=0 3'pad=0 strand=- repeatMasking=none
agtgttctcaagggaccgctctacgacgccatgctttgcatactaaagag
catggatttactagttacctgtgtaatcttcagtaaacgatttaacttct
ctgtgcttcagttatctcatctataaaatagagatcagtgaactaatcc
cagtaaaatgaataccattaagtgacactgattatcagttacttcacttg
cggaagagtggagggcatgactaggaatggggtggggaggagggagtcaaa
gaagtcttagctgaatttttttttttttttttttttttttgagacgaag
tctcgctctgtcgaccaggctggagtgcagtggtgcgatctcggctcact
gcaagctccgcctcccggttcacgccattctcctgcctcagcctcccga
gtagctgggactacaagcacccgccaccacgcctggctaattttttgtatt
tttagtagagacggggtttcaccgtgttagtcaggatggtctcgatctcc
cgacctcatgatccacccgcctcagcctcccaaagtgctgggattacagg
cgtgagcaaccgagcccggcccagctgtattttatacattaaaaaagaa
aagtatttaggtattcatacgtgggccgagttttctcctctctcatacaa
gcacattacacgcgaagccagattagttcatgaatgtgctactgcacggg
gtggctaagaaatcctgcttgcaaaccgctttgggtcctgcgtggagaat
ggtttcgagtgagagccgaaccctaaatccgtcttccttatgtggagctc
aacgcgactctcaggtattcaggaagaatacctttttgctcagcacctgcg
gagtggtggccacagcgaggcgctcgggagaggcgcctggaggccggcag
tgggggcgcgccgcctgagcaggggtgcggggcggggagaaggccggccc
acgtggaccgcggggccaggcagggacaggagcagccgggcggcccggcc
AATCAGCGCGTTCCGCGGCGGGCCCGGCCCCTCCTGGTCAGCGCGCTAGC
TGGGCTCGGCTCCGCACTGCTAGCTGCGCGCCGCCCTGGACGGGGCGCAC
CGACTGCGCGCGCGGCTGCGGGCAAACATCGGGAGTCCTGCCTCAGCTGC
CGCTTCTCCAGCAGCAGCTTCAGGCTTCTCCCGCAGGAGCTTCGGGCTTC
TCCTGGTAGAGACGTGGGAACTTTTCTTCTCCTGGCGAGGCTGCAGAGGT
GATGGGCCGCTCCCGGGGCTCCCGCGGGGAGGCGGCACGgtgagcgtcct
cgggctccggtgcggcgatcagtacctagttccggacgcgccggtccgac
ttggatgccggctctagtcgagtaagaagggttggaagggataaggaggg
gcgagaggatggggtgggggtggatttggaccctgtatttaggtgctgtc
tcgtgggcagccgctgcctctcggctggtaccgagttaactcagctcggt
gcagctcccctcatcccggctctctgggggcgccggggagagtgcctgtgc
tgaggtcggcgtgcaacccgaagttggaaggggcactccgaagtaaggat
gtgtggctggagagaggcagcggccgcttccagtttcggggttcatgtct
gacagaatcccgggggtgctctgctgatgcggaggaggccactcgatga
attggtataggggtggtgaactcaccgtgagctcttttctggacaagtc
gaccttagcgcttcatccctttaatctgagctaggatctttctaggagca
agcaggtgggagccggtcagcgtccccccgccccaccccaccctgaag
ctctggttgctaggatcttgcttgaagggcgcagcgagcgcttgggaggc
gtcttccagctgggagcgcaaagcttccgcccaagtggagaactggagc
gggtctggaagttgcgtctctttccgcgggaggcatctcagatttgccca
ccaaggtggcatctctacatttctttcgctcttttcccactttgccctg
ttaatccgctcctagaagagagggcatccttgaccctacgcaaggagctc
gggagaggattggaactggaaagcttgatctcctgcacctggtgaggctg
cccaagccagacacagtgcgctggtgcgttttcttctcgaatcagcatc
atttaacgtttaggggctccacggagccttagtaaagctgtgaatcagct
cctaagcagtatgtacatgcacgggttcacggactcgccgagacctagcc
tggtgcccatccccgtcaccgagattcagggacccccttttggtttaac
..intron 1................exon 2-6: GTCTTCTGAGC
TACGATAATTTTTTGGAACGGCAGAAATGATTGGTTCTAGCAACAGATGG

Figure 2B:

```
GAATTTGGAGTCACTCTGAAATATATCCTGGAATAAGTGTGTTTGACTAG
AACCACATCTTATGAGGTCCCCAAGGATGAGAGTCTGTGCTAAGTCAGTG
TTGCTGTCGCACTGGCTCTTTCTAGCCTACGTGTTAATGGTGTGCTGTAA
GCTGATGTCCGCCTCAAGCCAGCACCTCCGGGGACATGCAGGTCACCACC
AAATCAAGCAAGGGACCTGTGAGGTGGTCGCCGTGCACAGGTGCTGCAAT
AAGAACCGCATAGAAGAGCGGTCACAAACGGTCAAGTGCTCTTGCTTCCC
GGGACAGGTGGCGGGCACAACTCGGGCTCAACCTTCTTGTGTTGAAGCTT
CCATTGTGATTCAGAAATGGTGGTGTCACATGAATCCGTGTTTGGAAGGA
GAGGATTGTAAAGTGCTGCCAGATTACTCAGGTTGGTCCTGTAGCAGTGG
CAATAAAGTCAAAACTACGAAGGTAACGCGGTAGCGAAGAGAGAGGTGTG
CTTCAATCCTGGAGGGGCAGCAGGAGGCGGAGCTCTTTTGCTTGGATTCC
CATCATGGCCCCTTTGCAGAAAATTGTCTAGGATTTCAGCAACTTCATAT
TTGTATATGTGAGCTGTGAGAGGTGGCATTCACTTAACTGGCCCAGCCCT
CTCTGCTTCGTGATTTTATTTCATTGAATTATAACCACAAGCCACCACCC
ATTTGACATCCTCTCTGGATTCCCAAGGAGCATACCTCCAAAATCCGAGA
AGAGCAAATCAGAGTCTTCAAAATGGATCACCACTAAGGGCATGTTCATT
CTTCACTTTCTTTCTGCTTTTACAAAAGAACTTGGATGTATGTTCCAAAG
GGTCCTCATTCTGTTCCTCTTTTGAACTTTTCCTTTTGTCCTTGTATTAA
AGTGGTTTTAAAGGGGTCTAAAAAGATTTTGGCAAAACATATTTGCAGAT
GTAGATTAGCTGGTGAAGAAAATTACTGCTAGAGATCAACTGATTAACTG
GTAAAGAACGTTTATTTTATAACCCTTGAAGAATAGAAGGACATAGTTGG
ATTATTGTGTGTGCATTGTATTTTTACTTCTATTTTTTTTTGCTTTCCA
TTTTCCAGTTAGCAGAGATAAAATGAGAGCGTTTTAACTTCAATGTACCA
TTTTACTGAGTGCTAAGGAAGCATATCAATTCCAATATTTTATAACCAAA
GCTCTATCAGAACATATTTATAAAACTTGTTGGAATTTTTACGGCTTTTG
TGTAGTCATGTAGGTAAATCATTTAAAATATAAAACAATCTCAATTTAGA
TCAAGGGTTATTTCTTAGATCAAATTTATGCCAATTATATGAAAAGATTT
TAACTCCGAGACAGGAGTCTTTCAGTGCTGAATTTTTAGACTGTAAATGA
GTTCTTCTTAACTTAGCTGTTTCCCTACTTCTGTGACTTCTGTGTTAGCC
ATCTTATTTCTTTAAAATCTGAGTCCTGATTGGCTTAATGATTTTGCAGC
AGACATGTCTCCACATATTCTCAAATGCTGTCATGCGGAAACGTATGAAA
CAGATGAAGAATGACTGACCCAGATTTTAGATGTATAATGTTGTTAAAGT
ACATACTACTGTAAAAATATGGGATGAATTTATATATTAAGAAATGCCA
AAAACATAGTTTCTGCACCAAGTTAATTATCCCTGTCCTTTCACATTTAT
AGGGGGAAAATAAATACTTTAATGTTGTTTATAGCCTAACAGTTATTTGA
TTTTATTCTTGCAGAGGGAATGGAAAGGAATGGAAAGATTTGTTGGCGTA
ATTTTTGAATATTTGTTATGATCATATGAATAAGTAAAAAAATTCATCCT
GCTGATGGCATA
```

Figure 4:

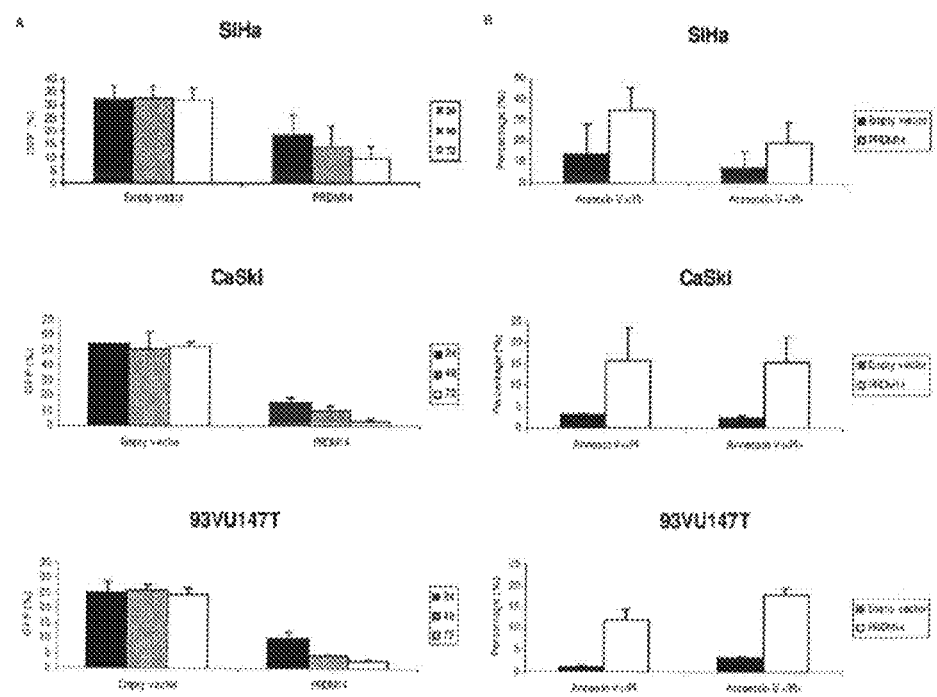

Figure 4. Effects of ectopic PRDM14 expression in SiHa, CaSki and 93VU147T cells. (A) The percentage of GFP+ cells declines in the PRDM14-transfected cells, compared to the empty vector cells, 24, 48 and 72 hours post-transfection. (B) Flow cytometry analysis of cells double labeled with Annexin V and PI shows an increase in both early (AnnexinV+/PI−) and late (AnnexinV+/PI+) apoptotic cells in the PRDM14 expressing cell population.

Figure 6: PRDM14 and FAM19A4 methylation levels in hrHPV-positive head and neck tissue specimens (HNSCC: Head-and-Neck SCC). Methylation levels are significantly increased in carcinomas compared to controls.

SEQUENCE LISTING

<160> NUMBER OF SEQ ID NOS: 10

<210> SEQ ID NO 1
<211> LENGTH: 24
<212> TYPE: DNA
<213> ORGANISM: Artificial
<220> FEATURE:
<223> OTHER INFORMATION: primer

<400> SEQUENCE: 1
ttattagcgg gttagacgtc gttt    24

<210> SEQ ID NO 2
<211> LENGTH: 18
<212> TYPE: DNA
<213> ORGANISM: Artificial
<220> FEATURE:
<223> OTHER INFORMATION: primer

<400> SEQUENCE: 2
cgtcccgaaa tcgaaccc    18

<210> SEQ ID NO 3
<211> LENGTH: 18
<212> TYPE: DNA
<213> ORGANISM: Artificial
<220> FEATURE:
<223> OTHER INFORMATION: primer

```
<400> SEQUENCE: 3
agtcgggcgg ttcggtta                                                    18

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
ccaaaaacga cgcgcaacta                                                  20

<210> SEQ ID NO 5
<211> LENGTH: 30
<212> TYPE: DNA
<213> ORGANISM: Artificial
<220> FEATURE:
<223> OTHER INFORMATION: probe

<400> SEQUENCE: 5
cttactctcc gctcccaatt cgaaaaatcc                                       30

<210> SEQ ID NO 6
<211> LENGTH: 17
<212> TYPE: DNA
<213> ORGANISM: Artificial
<220> FEATURE:
<223> OTHER INFORMATION: probe

<400> SEQUENCE: 6
cccaactaac gcgctaa                                                     17

<210> SEQ ID NO 7
<211> LENGTH: 2443
<212> TYPE: DNA
<213> ORGANISM: Homo sapiens

<400> SEQUENCE: 7
cccgccagct ttagggactc tggcggcgtc tcttagccgg gtagatgttc ctcctttccc      60
tctctcttcc aagccgctgc caggccgggg gtgaggctgc acctcagtct tcagccccga     120
aggccgcgcc cggggcgggt cgctccccat tcagctaaga ggaagcagcg gccgggggc      180 aggcgaggaa cctgtcccgg ctcacccggc aagactgcgt ttcccccacc ctcggcgctt     240
ctttctgtga atgtgaatgg aactaagcgt tcctttctct ccctcaatgg ccggcgagga     300
gaattcaaat gcggtctttg ggcgctcggt atgggtctgg accttggttt tcagagcctg     360
cgcgtccaag gtcgctagcc tttcccgaag gaagtgacag ctgcggcggc gcggaggcc      420 catcctcggt cgtttaaagc cacttaagga ataaaagccc ccgagagagc aaaacgacca     480
cccgaaacct cggaagcgtc gggggtgccg ggcccaacgc tcccacgtgt cactgccggg     540
gactcgcgag gcgaagcttc ccagcgctca aggcgctccc gcctcgtccc caggtatcag     600
gaacagacac ccaccaggtc caccagcggg tcagacgccg ccttcgggca ggctgggatc     660
ttccgaactg ggagcggaga gtaagggggct cgacccccggg acgcgagtcc ggccttctgg    720
actccggttc agggtgtgtg tgcgcgcgga ggggcttatc tgggggccct gggtagcaca     780
cgtgttcggt ttttttctcc ccgactccgc acgcctggag cggcaatact gcctgccta      840 gaaggccagc ggcgagtgct cgccactagg gtcccaggga gggtttggaa aactgatgag     900
ttaagtgagc gaccccaggg gacagagggc gagtcgagag tcggccaatg gctgcggtgg     960
```

```
gcggggagaa gacgacgcgg ggatctgcgt gggccgggtc aattccctac cctcgacctg    1020
tcgatgcccc gcggccccgc ccgccctctt aagcctggct cagccctcag ggcccgcccg    1080
aagtctaccg agcccgagtg gcctaccgag cccgagtggc cccgcagcgt ccaggaggcg    1140
cccgctccgc ggtggcgctc ttggaggtgg tgtcggaggt aggcacggga caggacgcgc    1200
ctggggcccg gggcggtggt cttccagggc cgttggggag gcggcagca ctcgctggcg     1260 cagttcgttt tggatggtcg ttctgccctc tcggggctt tgaatcccaa gttgcagatc     1320
cctgaggtcg gaggaggcta ggagaagggc gcctttggag gatcgggagg agacgggccg    1380
ctgcctgtgt cgtggctgac ctcttctcct gaccccgtgt tctttaattt ctgagtcatg    1440
accctgcttg gttttcttat tgggctcatt gatctcaaga cccgccggcc ctgaaggggc    1500
ttcattcttc agcctcggtg aacttgctgc ctgtctatta aaacgccatc ctttcccggc    1560
ggtgcggggg cgggaggact ggcagtcgcc gaggctcttc gctcccacct ggccagggct    1620
cgtccacgcg gctcccgagg ggctacccca ggccccaata gtcctggtag aatgattgga    1680
gtttccgagg aacccgggga atgtggcgga cgctgcccgc gagggaaaag aggttcaggc    1740
ggcgcatcct agggcagcca aaagtggcgc gcccctcccc tgcgggcagt caggaccgcc    1800
aggacccgcg gggtcacacc gctgggccag agcaggtcgc ggggtccctg gacctgcccg    1860
ggggctctgg gagcgcgtct ccatctgcgc ggtgcgaccc agggtcctcg gctcttccct    1920
cccagccgag ggcccaggag cgcctggagc tgtcgcttgc tccattgccc tccgaccgcc    1980
tgcgctcggc tcccggccca gccccgaggt tggcagggcc ccgcggctcc cacagaccct    2040
accaacgagt tttgtaggac tgagaagaag gaaggaaagg gaacttcaat gggttttgca    2100
ggaaccgggt tggggccga aagcggagag cgggtgtggg aaggcggccg ggcttaggga     2160
aggggtgctt ggagagggaa ggggaaggca acactaaccc ggaatttaga gtagggcagg    2220
atcccggcag atttccgttt ggggcttttt tgtgtttgct tctattgctg tttttttcgtt   2280 ttgtcttaat tgtgggagcg ggctggcggg atcggactgg gggcgtttat cctgttccct    2340
tggatctggg gctggctggg gtggaggagg ctggtgggga ggcgcgggtc ggaccccggg    2400
aagctcccgc gcggtgtcct cagcggcgcc cgcttttctg cag                       2443

<210> SEQ ID NO 8
<211> LENGTH: 2166
<212> TYPE: DNA
<213> ORGANISM: Homo sapiens

<400> SEQUENCE: 8
agccgccgag cgtgcggtcc cgggatggct ctaccccggc caagtgaggc cgtgcctcag     60
gacaaggtgt gctacccgcc ggagagcagc ccgcagaacc tggccgcgta ctacacgcct    120
ttcccgtcct atggacacta cagaaacagc ctggccaccg tggaggaaga cttccaacct    180
ttccggcagc tggaggccgc agcgtctgct gcccccgcca tgcccccctt ccccttccgg    240
atggcgcctc ccttgctgag cccgggtctg gcctacagag gggagcctct ctacgatctg    300
ccctggtaca gcaagctgcc accgtggtac ccaattcccc acgtcccag  ggaagtgccg    360 cccttcctga gcagcagcca cgagtacgcg ggtgccagca gtgaagatct gggccaccaa    420
atcattggtg gcgacaacga gagtggcccg tgttgtggac ctgacacttt aattccaccg    480 cccccctgcgg atgcttctct gttacctgag gggctgagga cctcccagtt attaccttgc    540
tcacccagca agcagtcaga ggatggtccc aaaccctcca accaagaagg gaagtcccct    600
```

```
gctcggttcc agttcacgga ggaggacctg cacttcgttc tgtacggggt cactcccagc      660
ctggagcacc cagccagcct gcaccatgcg atttcaggcc tcctggtccc cccagacagc      720
tctggatctg attctcttcc tcaaactctg gataaagact cccttcaact tccagaaggt      780
ctatgcctca tgcagacggt gtttggtgaa gtcccacatt ttggtgtgtt ctgcagtagt      840
tttatcgcca aaggagtcag gtttgggccc tttcaaggta aagtggtcaa tgccagtgaa      900
gtgaagacct acggagacaa ttctgtgatg tgggagatct ttgaagatgg tcatttgagc      960
cactttatag atggaaaagg aggtacgggg aactggatgt cctatgtcaa ctgtgcccgc     1020
ttccccaagg agcagaacct agttgctgtg cagtgtcaag ggcatatatt ttatgagagc     1080
tgcaaagaga tccatcagaa ccaagagctc cttgtgtggt atggagactg ctatgagaaa     1140
tttctggata ttcctgtgag ccttcaggtc acagagccgg ggaagcagcc atctgggccc     1200
tctgaagagt ctgcagaagg ctacagatgt gaaagatgtg ggaaggtatt tacctacaaa     1260
tattacagag ataagcacct caagtacacc ccctgtgtgg acaagggcga taggaaattt     1320
ccctgttctc tctgcaaacg atcctttgag aagcgggacc ggcttcggat ccacattctt     1380
catgttcatg agaagcaccg gcctcacaag tgttctacat gtgggaaatg tttctctcaa     1440
tcttccagcc taaacaaaca catgcgagtc cactctggag acagaccata ccagtgtgtg     1500
tattgtacta gagaggttcac agcctccagc atactccgca cacacatcag gcagcactcc     1560
ggggagaagc ccttcaaatg caagtactgt ggtaaatctt ttgcatccca tgctgcccat     1620
gacagccatg tccggcgttc acacaaggag gatgatggct gctcatgcag catctgtggg     1680
aaaatcttct cagatcaaga acattctac tcccacatga agtttcatga agactactag     1740
ccctgccagg cacaatgact cacgcctgta atcccagcac tttgggaggc agaggtgggt     1800
ggatcactca gtccaggag ttcgagacca gcctgggcaa catggtgaaa tcctgtctct     1860
accaaaaaaa tacaaaaatc agctgggggt ggtggcacat gcctgtggtt ccagccactc     1920
aggaggtcga ggtggcagga tggtttgagc acaggagacg gaggttgctg tgagctgaga     1980 tcgcccccact gcttttcaac ctgggtgaca gaaccagacc ctgtctcaaa acaaaacaaa     2040 acaaaaaaaaa tgagtagccc tcaagagtgt ggagacaatg taaaaacaag agattcggat     2100
tctctctatt tccttttatg ggttatagaa gtccctgcag ttggctgtgt gtggtggctc     2160
acgcct                                                                2166
```

<210> SEQ ID NO 9
<211> LENGTH: 2350
<212> TYPE: DNA
<213> ORGANISM: Homo sapiens

<400> SEQUENCE: 9

```
agtgttctca agggaccgct ctacgacgcc atgctttgca tactaaagag catggattta       60
ctagttacct gtgtaatctt cagtaaacga tttaacttct ctgtgcttca gttatctcat      120
ctataaaata gagatcagat gaactaatcc cagtaaaatg aataccatta agtgacactg      180
attatcagtt acttcacttg cggaagagtg gagggcatga ctaggaatgg ggtgggagga      240
gggagtcaaa gaagtcttag ctgaattttt ttttttttt tttttttttt tgagacgaag      300
tctcgctctg tcgaccaggc tggagtgcag tggtgcgatc tcggctcact gcaagctccg      360
cctccccggt tcacgccatt ctcctgcctc agcctcccga gtagctggga ctacaagcac      420
ccgccaccac gcctggctaa ttttttgtatt tttagtagag acggggtttc accgtgttag      480
tcaggatggt ctcgatctcc cgacctcatg atccacccgc ctcagcctcc caaagtgctg      540
```

```
ggattacagg cgtgagcaac cgagcccggc cccagctgta ttttatacat taaaaaagaa    600
aagtatttag gtattcatac gtgggccgag ttttctcctc tctcatacaa gcacattaca    660
cgcgaagcca gattagttca tgaatgtgct actgcacggg gtggctaaga aatcctgctt    720
gcaaaccgct ttgggtcctg cgtggagaat ggtttcgagt gagagccgaa ccctaaatcc    780
gtcttcctta tgtggagctc aacgcgactc tcaggtattc aggaagaata ccttttgctc    840
agcacctgcg gagtggtggc cacagcgagg cgctcgggag aggcgcctgg aggccggcag    900
tgggggcgcg ccgcctgagc aggggtgcgg ggcggggaga aggccggccc acgtggaccg    960
cggggccagg cagggacagg agcagccggg cggcccggcc aatcagcgcg ttccgcggcg   1020
ggcccggccc ctcctggtca gcgcgctagc tgggctcggc tccgcactgc tagctgcgcg   1080
ccgcccggga cggggcgcac cgactgcgcg cgcggctgcg ggcaaacatc gggagtcctg   1140
cctcagctgc cgcttctcca gcagcagctt caggcttctc ccgcaggagc ttcgggcttc   1200
tcctggtaga gacgtgggaa cttttcttct cctggcgagg ctgcagaggt gatgggccgc   1260
tcccggggct cccgcgggga ggcggcacgg tgagcgtcct cgggctccgg tgcggcgatc   1320
agtacctagt tccggacgcg ccggtccgac ttggatgccg gctctagtcg agtaagaagg   1380
gttggaaggg ataaggaggg gcgagaggat ggggtggggg tggatttgga ccctgtattt   1440
aggtgctgtc tcgtgggcag ccgctgcctc tcggctggta ccgagttaac tcagctcggt   1500
gcagctcccc tcatcccggc tctctggggc gccggggaga gtgcctgtgc tgaggtcggc   1560
gtgcaacccg aagttggaag gggcactccg aagtaaggat gtgtggctgg agagaggcag   1620
cggccgcttc cagtttcggg gttcatgtct gacagaatcc ccggggtgc tctgctgatg   1680 cggaggaggc cactcgatga attggtatag ggggtggtga actcaccgtg agctcttttc   1740
tggacaagtc gaccttagcg cttcatccct ttaatctgag ctaggatctt tctaggagca   1800
agcaggtggg agccggtcag cgtcccccg ccccaccccc accctgaag ctctggttgc   1860 taggatcttg cttgaagggc gcagcgagcg cttgggaggc gtcttccagc tgggagcgca   1920
aagcttcccg cccaagtgga gaactggagc gggtctggaa gttgcgtctc tttccgcggg   1980
aggcatctca gatttgccca ccaaggtggc atctctacat ttctttcgct cttttcca     2040 ctttgccctg ttaatccgct cctagaagag agggcatcct tgaccctacg caaggagctc   2100
gggagaggat tggaactgga aagcttgatc tcctgcacct ggtgaggctg cccaagccag   2160
acacagtgcc gctggtgcgt tttcttctcg aatcagcatc atttaacgtt taggggctcc   2220
acggagcctt agtaaagctg tgaatcagct cctaagcagt atgtacatgc acgggttcac   2280
ggactcgccg agacctagcc tggtgcccat cccccgtcac cgagattcag ggaccccct   2340 ttggtttaac                                                          2350
```

<210> SEQ ID NO 10
<211> LENGTH: 1923
<212> TYPE: DNA
<213> ORGANISM: Homo sapiens

<400> SEQUENCE: 10

```
gtcttctgag ctacgataat ttttggaac ggcagaaatg attggttcta gcaacagatg      60
ggaatttgga gtcactctga aatatatcct ggaataagtg tgtttgacta gaaccacatc    120
ttatgaggtc cccaaggatg agagtctgtg ctaagtcagt gttgctgtcg cactggctct    180
ttctagccta cgtgttaatg gtgtgctgta agctgatgtc cgcctcaagc cagcacctcc    240
```

```
ggggacatgc aggtcaccac caaatcaagc aagggacctg tgaggtggtc gccgtgcaca      300
ggtgctgcaa taagaaccgc atagaagagc ggtcacaaac ggtcaagtgc tcttgcttcc      360
cgggacaggt ggcgggcaca actcgggctc aaccttcttg tgttgaagct tccattgtga      420
ttcagaaatg gtggtgtcac atgaatccgt gtttggaagg agaggattgt aaagtgctgc      480
cagattactc aggttggtcc tgtagcagtg gcaataaagt caaaactacg aaggtaacgc      540
ggtagcgaag agagaggtgt gcttcaatcc tggaggggca gcaggaggcg gagctctttt      600
gcttggattc ccatcatggc cccttttgcag aaaattgtct aggatttcag caacttcata    660
tttgtatatg tgagctgtga gaggtggcat tcacttaact ggcccagccc tctctgcttc     720
gtgattttat ttcattgaat tataaccaca agccaccacc catttgacat cctctctgga     780
ttcccaagga gcatacctcc aaaatccgag aagagcaaat cagagtcttc aaaatggatc     840
accactaagg gcatgttcat tcttcacttt ctttctgctt ttacaaaaga acttggatgt     900
atgttccaaa gggtcctcat tctgttcctc ttttgaactt ttccttttgt ccttgtatta     960
aagtggtttt aaagggtct aaaaagattt tggcaaaaca tatttgcaga tgtagattag    1020
ctggtgaaga aaattactgc tagagatcaa ctgattaact ggtaaagaac gtttatttta    1080 taaccttga agaatagaag gacatagttg gattattgtg tgtgcattgt attttactt     1140 ctattttttt tttgctttcc attttccagt tagcagagat aaaatgagag cgttttaact    1200
tcaatgtacc attttactga gtgctaagga agcatatcaa ttccaatatt ttataaccaa    1260
agctctatca gaacatattt ataaaacttg ttggaattt tacggctttt gtgtagtcat     1320
gtaggtaaat catttaaaat ataaaacaat ctcaatttag atcaagggtt atttcttaga    1380
tcaaatttat gccaattata tgaaaagatt ttaactccga gacaggagtc tttcagtgct    1440 gaattttag actgtaaatg agttcttctt aacttagctg tttccctact tctgtgactt     1500
ctgtgttagc catcttattt ctttaaaatc tgagtcctga ttggcttaat gattttgcag    1560
cagacatgtc tccacatatt ctcaaatgct gtcatgcgga aacgtatgaa acagatgaag    1620
aatgactgac ccagatttta gatgtataat gttgttaaag tacatactac tgtaaaaata    1680
tgggatgaat tttatatatt aagaaatgcc aaaaacatag tttctgcacc aagttaatta    1740
tccctgtcct ttcacattta taggggggaaa ataaatactt taatgttgtt tatagcctaa   1800
cagttatttg attttattct tgcagaggga atggaaagga atggaaagat ttgttggcgt    1860
aatttttgaa tatttgttat gatcatatga ataagtaaaa aaattcatcc tgctgatggc    1920
ata                                                                  1923
```

PRDM14 AND FAM19A4, MOLECULAR DIAGNOSTIC MARKERS FOR HPV-INDUCED INVASIVE CANCERS AND THEIR HIGH-GRADE PRECURSOR LESIONS

CROSS REFERENCE TO RELATED APPLICATIONS

This application claims the priority of PCT/NL2013/050729, filed on Oct. 14, 2013, which claims priority to European Application No. 12188377.1, filed Oct. 12, 2012, the entire contents of each of which are hereby incorporated in total by reference.

SEQUENCE LISTING

This application incorporates by reference the Sequence Listing contained in an ASCII text file named "362346_00023_ST25.txt" submitted via EFS-Web. The text file was created on Apr. 10, 2015, and is 14 kb in size

FIELD OF THE INVENTION

The invention relates to the field of cancer prevention and medical diagnostics; and is concerned with a molecular diagnostic marker for human papillomavirus (HPV)-induced invasive cancers and high-grade precursor lesions thereof, such as invasive cervical cancer and premalignant cervical lesions. In particular, the present invention relates to the use of the PRDM14 and FAM19A4 genomic and regulatory sequence as marker for hrHPV-induced premalignant lesions with invasive potential and hrHPV-induced invasive cancers.

BACKGROUND OF THE INVENTION

Cancer of the uterine cervix is the third most common cancer in women world-wide and is responsible for approximately 250.000 cancer deaths a year.

Cervical squamous cell carcinoma development is characterized by a sequence of premalignant lesions, so-called cervical intraepithelial neoplasia (CIN), which are graded 1 to 3, referring to mild dysplasia (CIN 1), moderate dysplasia (CIN 2) and severe dysplasia/carcinoma in situ (CIN 3), respectively. CIN 1 is also referred to as low grade squamous intraepithelial lesion (LSIL) and CIN 2 and CIN 3 together as high grade squamous intraepithelial lesion (HSIL). For cervical adenocarcinoma, adenocarcinoma in situ (ACIS) is an established precursor lesion. In principle, these premalignant lesions are reversible, although the more severe the lesion, the lower the chance of spontaneous regression. Cervical cancer is considered a preventable disease because the premalignant stages can be detected by exfoliative cytology and treated relatively easily when necessary, with only minor side effects. Cervical screening is aimed to early diagnose the high-grade premalignant (i.e., CIN 2/3 and adenocarcinoma in situ) and treatable cancerous lesions, thereby reducing the mortality of invasive cervical cancer. General medical practice comprises the treatment of all women with morphologically confirmed CIN 2, CIN 3 and adenocarcinoma in situ, in order to prevent the development of cervical cancer.

Over the past decade it has been well established that cervical carcinogenesis is initiated by an infection with high-risk human papillomavirus (hrHPV). Expression of the viral oncogenes E6 and E7, which disturb the p53 and Rb tumor suppressor pathways, respectively, has been shown to be essential for both the onset of oncogenesis and the maintenance of a malignant phenotype. Therefore, testing for hrHPV appeared as an attractive, primary screening tool. However, consistent with a multistep process of carcinogenesis, additional alterations in the host cell genome are required for progression of an hrHPV infected cell to invasive cancer cell. Only a small proportion of women infected with high-risk HPV will develop high-grade premalignant cervical lesions (CIN 2/3) and, if left untreated, cervical cancer. In most women with premalignant cervical lesions the lesions regress spontaneously. Of the women who participate in population based screening, about 5-6% have a positive hrHPV test. However, only at maximum 20% of them (1% of the participating women) have ≥CIN 2/3. Therefore, primary screening by hrHPV testing will be accompanied with a substantial number of redundant follow-up procedures and unnecessary anxiety amongst women, unless markers can be applied to the cervical smears that allow stratification of hrHPV positive women for risk of ≥CIN 2/3 and ≥adenocarcinoma in situ.

A major challenge is to reduce the percentage of HPV test positive women to those that have clinically meaningful lesions. One mode is to use cytology as a secondary (so-called triage) test for hrHPV positive women. Still, this leaves a substantial number of hrHPV positive women with normal cytology (3.5% of the women in the screening population), of which still 10% have or acquire ≥CIN 3. Moreover, cytology is not an option for self-sampled cervico-vaginal specimens that can be taken at home, since these are not representative for the cytological status of the cervix. Another mode is to use HPV16/18 genotyping. This however leaves women with non-HPV16/18 types who are, although to a lesser extent, also at risk of ≥CIN 2/3 and ≥adenocarcinoma in situ. Therefore, there is a need for supplementary or alternative triage tools to stratify hrHPV positive women into those with and without ≥CIN 2/3 and ≥adenocarcinoma in situ.

SUMMARY OF THE INVENTION

The inventors now have found a method for detecting HPV-induced high-grade precancerous lesions and HPV-induced invasive cancers, wherein said method comprises the detection of hypermethylation in the PRDM14 and/or FAM19A4 gene in a cell whereby such hypermethylation indicates the presence of HPV-induced precursor lesions with invasive potential and HPV-induced invasive cancers. Preferably, in such a method said HPV-induced high-grade precancerous lesion or HPV-induced invasive carcinoma is a high-grade premalignant cervical lesion or invasive cervical cancer, more preferably a high-risk HPV-induced invasive cancer.

In a preferred embodiment of the invention the hypermethylation is detected in the CpG rich sequences as indicated in FIGS. 1 and 2.

The invention also relates to a method as defined above wherein said hypermethylation is an increased methylation of PRDM14 and/or FAM19A4 CpG rich promoter and/or genomic sequences in the test cell as compared to the comparable normal cell.

In a preferred embodiment of the invention the detection of (hyper)methylation is performed by using a methylation sensitive restriction endonuclease, chosen from the group consisting of BssHII, MspI, NotI and HpaII. In an alternative preferred embodiment of the invention, the detection of (hyper)methylation is performed via a methylation specific PCR, which is based on bisulfite modification of DNA, followed by specific PCR reactions that target CpG rich sequences. Preferably in such a method a nucleic acid probe or primer is used that binds to the nucleic acid as indicated in FIG. 1 or 2, and more preferably said nucleic acid probe or primer has a detectable label.

In another embodiment of the invention the nucleic acid probe has a nucleotide sequence selected from the group consisting of;
  a) a polynucleotide sequence capable of hybridizing under stringent conditions to the sequence PRDM14 as set forth in FIG. 1 or to the sequence FAM19A4 as set forth in FIG. 2;
  b) a polynucleotide having at least 70% identity to the polynucleotide of a);
  c) a polynucleotide complementary to the polynucleotide of a); and
  d) a polynucleotide comprising at least 15 bases of a nucleotide of a) or b).

Further preferred in the present method of the invention is the determination of the methylation of both the PRDM14 and the FAM19A4 gene. Also preferred is a combined detection of methylation of FAM19A4 and hsa-miR-124-2.

Also part of the invention is the use of PRDM14 and/or FAM19A4 as a molecular diagnostic marker for the detection of HPV-induced high-grade precancerous lesion or HPV-induced invasive carcinoma. Preferably, in such a use the methylation of said marker is predictive for the occurrence of said lesion or carcinoma.

The invention also comprises a kit of parts for use in a method of detecting HPV-induced high-grade precancerous lesion or HPV-induced invasive carcinoma, said kit comprising
  means for the detection of PRDM14 and/or FAM19A4 methylation wherein said means comprise probes and/or primers specific for the PRDM14 nucleotide sequence of FIG. 1 and/or the FAM19A4 nucleotide sequence of FIG. 2 and
  means for the detection of HPV infection, wherein said means comprise probes and primers specific for HPV.

BRIEF DESCRIPTION OF THE DRAWINGS

FIGS. 1A and 1B shows the PRDM14 5' regulatory region, coding sequence, CpG rich part of first intronic sequence and transcribed 3' non-coding sequences. Transcription start is indicated in bold, coding sequence is in upper case. A promoter sequence of 1000 bp and intron 1, both containing CpG rich sequences, are in lower case.

FIGS. 2A and 2B shows the FAM19A4 5' regulatory region, coding sequence, CpG rich part of first intronic sequence and transcribed 3' non-coding sequences. Transcription start is indicated in bold, coding sequence is in upper case. A promoter sequence of 1000 bp and intron 1, both containing CpG rich sequences, are in lower case.

FIG. 4. Effects of ectopic PRDM14 expression in SiHa, CaSki and 93VU147T cells. (A) The percentage of GFP$^+$ cells declines in the PRDM14-transfected cells, compared to the empty vector cells, 24, 48 and 72 hours post-transfection. (B) Flow cytometry analysis of cells double labelled with Annexin V and PI shows an increase in both early (AnnexinV$^+$/PI$^-$) and late (AnnexinV$^+$/PI$^+$) apoptotic cells in the PRDM14 expressing cell population.

DETAILED DESCRIPTION OF THE INVENTION

Figure 3:
FIG. 3 shows that the mRNA expression of PRDM14 in SiHa cervical cancer cells can be upregulated upon treatment with a DNA methylation inhibitor (DAC). Treatment of SiHa cervical cancer cells was performed with the methylation inhibitor 2'-deoxy-5'azacytidine (5'-aza or DAC) at 0.2 µM and 5 µM concentration. Other treatments were PBS and ethanol (EtOH). All treatments were in duplicate. Controls are human reference RNA and a -RT control (without reverse transcriptase added to the cDNA reaction mixture).

The term "HPV-induced invasive cancer" refers to a carcinoma induced by high-risk HPV, which invades surrounding tissue. This includes all HPV-induced carcinoma histotypes, i.e., squamous cell carcinomas, adenocarcinomas, adenosquamous carcinomas and neuroendocrine carcinomas. in relevant organs such as cervix, oral cavity, oropharynx, anus, rectum, penis, vulva, vagina, etc. It especially includes head and neck squamous cell carcinomas (HNSCC), cervical squamous cell carcinomas and cervical adenocarcinomas.

The term "invasive cervical cancer" refers to a cervical carcinoma invading surrounding tissue. This includes all carcinoma histotypes, i.e., squamous cell carcinomas, adenocarcinomas, adenosquamous cell carcinomas and neuroendocrine carcinomas.

The terms "premalignant lesion" and "precursor lesion" refer to a stage in the multistep cellular evolution to cancer with a strongly increased chance to progress to a carcinoma. With classical morphology the pathologist is unable to predict in the individual patient which of these lesions will progress or regress. The current patent refers to a method, which can predict invasive cancer or a high-grade precursor lesion thereof.

The term "high-grade premalignant cervical lesion" refers to a stage in the multistep cellular evolution to cervical cancer with a strongly increased chance to progress to a cervical carcinoma. The term "capable of specifically hybridizing to" refers to a nucleic acid sequence capable of specific base-pairing with a complementary nucleic acid sequence and binding thereto to form a nucleic acid duplex.

The term "advanced CIN3 lesion" is used for a histotyped CIN3 lesion with a long-term preceding hrHPV infection resulting in significantly more DNA copy number alterations. Accordingly, this subcategory of CIN3 lesions represents a higher disease stage at increased cancer risk.

A "complement" or "complementary sequence" is a sequence of nucleotides which forms a hydrogen-bonded duplex with another sequence of nucleotides according to Watson-Crick base-paring rules. For example, the complementary base sequence for 5'-AAGGCT-3' is 3'-TTCCGA-5'.

The term "stringent hybridization conditions" refers to hybridization conditions that affect the stability of hybrids, e.g., temperature, salt concentration, pH, formamide concentration and the like. These conditions are empirically optimised to maximize specific binding and minimize non-specific binding of the primer or the probe to its target nucleic acid sequence. The terms as used include reference to conditions under which a probe or primer will hybridise to its target sequence, to a detectably greater degree than other sequences (e.g. at least 2-fold over background). Stringent conditions are sequence dependent and will be different in different circumstances. Longer sequences hybridise specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength and pH) at which 50% of a complementary target sequence hybridises to a perfectly matched probe or primer. Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" include hybridization with a buffer solution of 30% formamide, 1 M NaCl, 1% SDS at 37° C. and a wash in 2×SSC at 40° C. Exemplary high stringency conditions include hybridization in 50% formamide, 1 M NaCl, 1% SDS at 37° C., and a wash in 0.1×SSC at 60° C. Hybridization procedures are well known in the art and are described in e.g. Ausubel et al, Current Protocols in Molecular Biology, John Wiley & Sons Inc., 1994.

The term "oligonucleotide" refers to a short sequence of nucleotide monomers (usually 6 to 100 nucleotides) joined by phosphorous linkages (e.g., phosphodiester, alkyl and aryl-phosphate, phosphorothioate), or non-phosphorous linkages (e.g., peptide, sulphamate and others). An oligonucleotide may contain modified nucleotides having modified bases (e.g., 5-methyl cytosine) and modified sugar groups (e.g., 2'-O-methyl ribosyl, 2'-O-methoxyethyl ribosyl, 2'-fluoro ribosyl, 2'-amino ribosyl, and the like). Oligonucleotides may be naturally-occurring or synthetic molecules of double- and single-stranded DNA and double- and single-stranded RNA with circular, branched or linear shapes and optionally including domains capable of forming stable secondary structures (e.g., stem-and-loop and loop-stem-loop structures).

The term "primer" as used herein refers to an oligonucleotide which is capable of annealing to the amplification target allowing a DNA polymerase to attach thereby serving as a point of initiation of DNA synthesis when placed under conditions in which synthesis of primer extension product which is complementary to a nucleic acid strand is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxy ribonucleotide. The primer must be sufficiently long to prime the synthesis of extension products in the presence of the agent for polymerization. The exact lengths of the primers will depend on many factors, including temperature and source of primer. A "pair of bi-directional primers" as used herein refers to one forward and one reverse primer as commonly used in the art of DNA amplification such as in polymerase chain reaction (PCR) amplification.

The term "probe" refers to a single-stranded oligonucleotide sequence that will recognize and form a hydrogen-bonded duplex with a complementary sequence in a target nucleic acid sequence analyte or its cDNA derivative.

DNA methylation is a biochemical process that is important for normal development in higher organisms. It involves the addition of a methyl group to the 5 position of the cytosine pyrimidine ring or the number 6 nitrogen of the adenine purine ring. DNA methylation at the 5 position of cytosine has the specific effect of reducing gene expression and has been found in every vertebrate examined. In adult somatic tissues, DNA methylation typically occurs in a CpG dinucleotide context.

Using a genome wide DNA methylation screen it has now been found that the gene encoding PR domain zinc finger protein 14 (further referred to as PRDM14; Genbank Accession NM_024504.2) and the gene encoding family with sequence similarity 19 (chemokine (C-C motif)-like), member A4 (further referred to as FAM19A4; Genbank Accession NM_001005527.2) are targeted by DNA methylation in primary keratinocytes following viral oncogene (HPV16E6E7) expression, and that PRDM14 and FAM19A4 promoter methylation are important determinants of hr-HPV induced carcinogenesis. The PRDM14 and FAM19A4 genomic and regulatory sequences thus provide valuable markers to diagnose invasive cervical cancer and the high-grade precursor lesions thereof. Additionally, the present invention is suited to diagnose non-cervical hrHPV-associated invasive cancers and their high-grade precursor lesions.

Cervical cancer is almost exclusively associated with human papillomavirus (HPV) infection. Human papillomaviruses, constitute a group of more than 100 types of viruses, as identified by variations in DNA sequence. The various HPVs cause a variety of cutaneous and mucosal diseases. HPVs are broadly classified into low-risk and high-risk types, based on their ability to induce malignant changes in infected cells. Low risk HPV types such as 1, 2, 4, 6, 11, 13 and 32 are primarily associated with benign lesions or common warts, while the high risk types, such as 16, 18, 31, 33, 35, 39, 45, 51, 52, 56, 58, 59, 66, and 68 are primarily associated with premalignant and malignant epithelial lesions. These high-risk types of HPV cause growths that are usually flat and nearly invisible, as compared with the warts caused by low-risk types, e.g. HPV-6 and HPV-11. The high-risk HPV types have been found to cause invasive carcinoma of the uterine cervix, as well as invasive carcinoma elsewhere in the anogenital tract and/or head-neck region. Therefore, the present invention is not only suited to detect invasive cervical cancer and precursor stages thereof associated with PRDM14 and/or FAM19A4, but also other invasive cancers and corresponding precursor stages that are induced by HPV, particularly of the high-risk type. Thus, the present invention provides a method for the risk assessment of any HPV-induced high-grade premalignant lesion or invasive cancer.

Very suitable HPV-induced precursor lesions and invasive cancers in the context of the present invention are cervical precancerous lesions and invasive cervical cancers, but also precursor lesions and invasive cancers induced by high-risk HPV in other tissues such as oral cavity, oropharynx, anus, rectum, penis, vulva, vagina, etc.

A test cell may be a (pre)neoplastic cell, a proliferating cervical cell, or any other cell wherein the presence of an HPV-induced precursor lesion with invasive potential and HPV-induced invasive cancer associated with PRDM14 and/or FAM19A4 is to be detected.

The PRDM14 gene, encoding a 64 kDa nuclear protein, has originally been identified as an important regulator in the maintenance of human embryonic stem cells, being involved in self-renewal and differentiation (Chia et al., Nature 2010, 468: 316-320). PRDM14 has been described to function as an oncogenic protein in human lymphoid neoplasms (Dettman et al., Oncogene 2011, 30: 2859-73) as well as in breast cancers (Nishikawa et al., Cancer Res 2007, 67:9649-57). Moreover, PRDM14 promoter methylation has been detected in human breast cancers (Nishikawa et al., Cancer Res 2007, 67:9649-57). The FAM19A4 gene, encoding a 16 kDa secreted protein, has originally been identified by sequencing of a library of human cDNAs (Strausberg et al., PNAS, 2002, 99(26):16899-903). This gene is a member of the TAFA family which is composed of five highly homologous genes that encode small secreted proteins. These proteins contain conserved cysteine residues at fixed positions, and are distantly related to MIP-1alpha, a member of the CC-chemokine family. The TAFA proteins are predominantly expressed in specific regions of the brain, and are postulated to function as brain-specific chemokines or neurokines, that act as regulators of immune and nervous cells (Tom Tang et al., Genomics 2004, 83(4):727-34). Alternatively spliced transcript variants have been observed for this gene. A relation to cancer has not been described.

The present inventors have now established that PRDM14 and FAM19A4 methylation of CpG rich regions, such as the promoter and the first intron of both genes, is a frequent event in cervical carcinomas of both squamous cell carcinoma, adeno-sqamous carcinoma, adenocarcinoma and neuroendocrine carcinoma histotypes, and their high-grade precursor lesions. In vitro studies revealed a functional involvement of PRDM14 inactivation in cervical cancer development, as PRDM14 overexpression in cells of the HPV 16 containing cervical cancer cell lines SiHa and CaSki induced apoptosis. This indicates that PRDM14 functions as a tumor suppressor gene in cervical cancer, which is most remarkable in view of the fact that an oncogenic function for this protein has previously been described in lymphoid neoplasms and breast cancer cells (Dettman et al., Oncogene 2011, 30: 2859-73; Nishikawa et al., Cancer Res 2007, 67:9649-57). The exact function of FAM19A4 has not yet been defined.

Most interestingly, the present inventors have shown that hypermethylation of the PRDM14 and FAM19A4 promoter (and intronic sequences) can be detected in cervical scrape samples and that this feature is able to predict the presence of a high-grade CIN lesion or invasive carcinoma. In addition, PRDM14 and FAM19A4 promoter methylation could be detected in cervical-vaginal specimens collected by self-sampling and was found to be associated with the presence of an underlying high-grade CIN lesion or invasive cervical cancer.

Accordingly, the present invention provides a method for detecting HPV-induced high-grade precancerous lesions and HPV-induced invasive cancers, said method comprising detection of hypermethylation in the PRDM14 and/or FAM19A4 gene in a cell whereby such hypermethylation indicates the presence of HPV-induced precursor lesions with invasive potential and HPV-induced invasive cancers.

The test cell of the subject may comprise a cell from a sample of mucosal cells, such as cervical cells, and also other tissue such as oral cavity, oropharynx, penis, vulva, anus, rectum and other tissues wherein a precursor lesion or cancer associated with HPV is to be detected. All such samples may be used as a sample in a method of the present invention. Preferably, a sample of a patient's cells comprises cervical cells as test cells. The cervical cells may e.g. be presented as a histological or cytological specimen. Cytological specimens comprise conventional cervical smears as well as thin layer preparations of cervical specimens and cervico-vaginal or vaginal specimens collected by self-sampling.

A method of the present invention is particularly suited for the detection of high-grade precancerous lesions and invasive cancers associated with PRDM14 and/or FAM19A4 that are induced by high-risk HPVs. A method of detecting HPV-induced high-grade precancerous lesions with invasive potential and HPV-induced invasive cancers may comprise measuring the PRDM14 and/or FAM19A4 promoter and first intron.

FIG. 1 shows the CpG-rich promoter region and CpG-rich first intronic sequence of the PRDM14 gene as well as the coding sequence and transcribed 3' non-coding sequence.

FIG. 2 shows the CpG-rich promoter region, part of the CpG-rich first intronic sequence of the FAM19A4 gene as well as the coding sequence and transcribed 3' non-coding sequence.

Detection of methylation is performed on nucleic acid, such as DNA. The reagents that are used are typically a nucleic acid (DNA) probe or (PCR) primer or a restriction endonuclease, preferably a methylation sensitive restriction endonuclease for the detection of the presence of methyl groups on the test cell DNA.

The test cell component may be detected directly in situ or it may be isolated from other cell components by common methods known to those of skill in the art before contacting with the reagent (see for example, "Current Protocols in Molecular Biology", Ausubel et al. 1995. 4th edition, John Wiley and Sons; "A Laboratory Guide to RNA: Isolation, analysis, and synthesis", Krieg (ed.), 1996, Wiley-Liss; "Molecular Cloning: A laboratory manual", J. Sambrook, E. F. Fritsch. 1989. 3 Vols, 2nd edition, Cold Spring Harbour Laboratory Press)

Since the present invention shows that PRDM14 functions as a tumor suppressor gene and that a decreased level of PRDM14 transcription can be upregulated by the inhibition of DNA methylation, it is often desirable to directly determine whether the PRDM14 gene is hypermethylated. Similarly, it is also desirable to directly determine whether the FAM19A4 gene is hypermethylated. In particular, the cytosine rich areas termed "CpG islands", which are primarily situated in the 5' regulatory regions of genes are normally unmethylated. The term "hypermethylation" includes any methylation of cytosine at a position that is normally unmethylated in the PRDM14 or FAM19A4 gene sequence (e. g. the PRDM14 or FAM19A4 promoter, first exon and first intronic sequence, see FIGS. 1 and 2, respectively). DNA methylation can be detected by the following assays currently used in scientific research:

Methylation-Specific PCR (MSP), which is based on a chemical reaction of sodium bisulfite with DNA that converts unmethylated cytosines of CpG dinucleotides to uracil or UpG, followed by traditional PCR. However, methylated cytosines will not be converted in this process, and primers are designed to overlap the CpG site of interest, which allows one to determine methylation status as methylated or unmethylated.

Whole genome bisulfite sequencing, also known as BS-Seq, which is a high-throughput genome-wide analysis of DNA methylation. It is based on aforementioned sodium bisulfite conversion of genomic DNA, which is then sequenced on a Next-generation sequencing platform. The sequences obtained are then re-aligned to the reference genome to determine methylation states of CpG dinucleotides based on mismatches resulting from the conversion of unmethylated cytosines into uracil.

The HELP assay, which is based on restriction enzymes' differential ability to recognize and cleave methylated and unmethylated CpG DNA sites.

ChIP-on-chip assays, which is based on the ability of commercially prepared antibodies to bind to DNA methylation-associated proteins like MeCP2.

Restriction landmark genomic scanning, a complicated and now rarely-used assay based upon restriction enzymes' differential recognition of methylated and unmethylated CpG sites; the assay is similar in concept to the HELP assay.

Methylated DNA immunoprecipitation (MeDIP), analogous to chromatin immunoprecipitation, immunoprecipitation is used to isolate methylated DNA fragments for input into DNA detection methods such as DNA microarrays (MeDIP-chip) or DNA sequencing (MeDIP-seq).

Pyrosequencing of bisulfite treated DNA. This is sequencing of an amplicon made by a normal forward primer but a biotenylated reverse primer to PCR the gene of choice. The Pyrosequencer then analyses the sample by denaturing the DNA and adding one nucleotide at a time to the mix according to a sequence given by the user. If there is a mismatch, it is recorded and the percentage of DNA for which the mismatch is present is noted. This gives the user a percentage methylation per CpG island.

Molecular break light assay for DNA adenine methyltransferase activity—an assay that relies on the specificity of the restriction enzyme DpnI for fully methylated (adenine methylation) GATC sites in an oligonucleotide labeled with a fluorophore and quencher. The adenine methyltransferase methylates the oligonucleotide making it a substrate for DpnI. Cutting of the oligonucleotide by DpnI gives rise to a fluorescence increase.

Methyl Sensitive Southern Blotting is similar to the HELP assay, although uses Southern blotting techniques to probe gene-specific differences in methylation using restriction digests. This technique is used to evaluate local methylation near the binding site for the probe.

Hypermethylation preferably can be detected by restriction endonuclease treatment of the PRDM14 or FAM19A4 polynucleotide (gene) and Southern blot analysis. Any restriction endonuclease that includes CG as part of its recognition site and that is inhibited when the C is methylated, can be utilized. Methylation sensitive restriction endonucleases such as BssHII, MspI, NotI or HpaII, used alone or in combination, are examples of such endonucleases. Other methylation sensitive restriction endonucleases will be known to those of skill in the art.

An alternative preferred means to test for methylated sequences is a methylation specific PCR, which is also based on bisulfite modification of DNA, followed by specific PCR reactions that target CpG rich sequences.

For purposes of the invention nucleic acid probe specific for PRDM14 or FAM19A4 may be used to detect the presence of PRDM14 or FAM19A4 polynucleotide (using nucleic acid probe) in biological fluids or tissues. Oligonucleotide primers based on any coding sequence region and regulatory sequence region in the PRDM14 or FAM19A4 sequence are useful for amplifying DNA, for example by PCR.

When using PCR primers, nucleic acid probes or restriction endonucleases, the 5' regulatory region, first intronic sequence and coding sequence of the PRDM14 or FAM19A4 sequence (as specified in FIGS. 1 and 2 respectively) is analysed.

Any specimen containing a detectable amount of PRDM14 or FAM19A4 polynucleotide can be used. Preferred samples for testing according to methods of the invention include such specimens as (cervical or vaginal) scrapes, cervico-vaginal lavages or swabs, and/or (cervical) biopsies and the like. Although the subject can be any mammal, preferably the subject is human.

Diagnostic methods for the detection of disorders, include methods wherein a sample for testing is provided, which sample comprises a cell preparation from cervical or other tissue. Preferably such samples are provided as smears or other cytological samples.

A cell or tissue sample obtained from a mammal, preferably a human, is suitably pre-treated to allow contact between the cellular DNA of a test cell comprised in said sample with a reagent that detects PRDM14 or FAM19A4 and detects an alteration in the methylation of the PRDM14 or FAM19A4 gene as compared to that of a comparable normal cell. Samples may be mounted on a suitable support to allow observation of individual cells. Examples of well-known support materials include glass, polystyrene, polypropylene, polyethylene, polycarbonate, polyurethane, optionally provided with layers to improve cell adhesion and immobilization of the sample, such as layers of poly-L-lysine or silane. Cervical smears or biopsies may for instance be prepared as for the Papanicolaou (Pap) test or any suitable modification thereof as known by the skilled person, and may be fixed by procedures that allow proper access of the reagent to the target component. In certain embodiments of the invention the cytological specimens are provided as conventional smear samples or thin layer preparations of cervical cells or liquid based cytology samples or any other kind of preparation known to those of skill in the art. If storage is required, routine procedures use buffered formalin for fixation followed by paraffin embedding, which provides for a well-preserved tissue infrastructure. In order to allow for immunohistochemical or immunofluorescent staining, the antigenicity of the sample material must be retrieved or unmasked. One method of retrieving the antigenicity of formaldehyde cross-linked proteins involves the treatment of the sample with proteolytic enzymes. This method results in a (partial) digest of the material and mere fragments of the original proteins can be accessed by antibodies.

In one embodiment of a method of the invention an increased methylation of the PRDM14 and/or FAM19A4 promoter in the test cell is detected as compared to the comparable normal cell.

In another embodiment an assay measuring the increased methylation of the FAM19A4 promoter and intron sequences in combination with an increased methylation of the hsa-miR124-2 sequence is preferred because of an increased sensitivity.

The mature hsa-miR124 sequence (Accession number MIMAT0000422) is encoded by 3 individual premature microRNA sequences located at three different genomic regions, i.e. hsa-miR124-1 (Accession number MI0000443) at chromosome 8p23.1, hsa-miR124-2 (Accession number MI0000444) at chromosome 8q12.3 and hsa-miR124-3 (Accession number MI0000445) at chromosome 20q12.33 (Accession numbers as indicated on the miRNA database, miRBase (www.mirbase.org), Faculty of Life Sciences, University of Manchester).

The use of an assay of hsa-miR124 hypermethylation for methods of detecting or predicting the occurrence of HPV-induced high-grade precancerous lesions and HPV-induced invasive cancers in a (self)sample of a cervical smear has been described in WO 2013/039394 and Wilting et al. (Mol. Cancer 2010: 9, 167).

The present invention also provides a kit of parts as defined in the claims, for use in a method of detecting HPV-induced precursor lesions with invasive potential and HPV-induced invasive cancers associated with PRDM14 and/or FAM19A4 in test cells of a subject. Such a kit may suitably comprise a brush or spatula to take a (cervical) scrape together with a container filled with collection medium to collect test cells. Alternatively, a sampling device consisting of an irrigation syringe, a disposable female urine catheter and a container with irrigation fluid will be included to collect cervical cells by cervico-vaginal lavage. A kit according to the present invention may comprise primers and probes for the detection of PRDM14 and/or FAM19A4 promoter methylation.

A kit of parts according to the invention comprises means for the detection of PRDM14 and/or FAM19A4 promoter methylation, such as, methylation-sensitive restriction enzymes, or probes or primers capable of hybridising to the nucleotide sequence of FIG. 1 and/or FIG. 2. Of course, when the assay is also meant to detect methylation of hsa-miR124-2, primers and probes for the detection of methylation in this sequence may be included.

In yet another alternative embodiment of a kit of the invention the means for the detection of PRDM14 and/or FAM19A4 promoter methylation may be combined with means for the detection of HPV infection, preferably for the detection of HPV infection of the high-risk type. Such means may comprise HPV-specific primers or probes, protein markers for HPV infection or even surrogate markers for HPV infection as are known in the art.

The present invention will now be illustrated by way of the following, non limiting examples.

EXAMPLES

Example 1

Discovery of PRDM14 and FAM19A4 as Methylation Targets in HPV-Induced Transformation A comprehensive analysis of genome-wide DNA methylation changes associated with HPV-induced transformation in vitro has been conducted (viral oncogene expression and subsequent immortalization of primary keratinocytes) by means of Methylation Specific Digital Karyotyping (MSDK) (Hu et al 2005). MSDK is a sequence based method that relies on cleavage of genomic DNA with a methylation sensitive restriction enzyme (AscI), thereby allowing unbiased comprehensive methylation profiling. In this method 21 bp sequence tags derived from specific locations in the genome are concatenated and analysed by high throughput sequencing. We determined genome-wide DNA-methylation changes resulting from expression of HPV16 E6 and E7, by comparing methylation patterns of untransduced primary foreskin keratinocytes (passage 5) to their early passage counterparts transduced with HPV16E6E7 (passage 7). Additionally, altered methylation associated with the acquisition of immortality, a critical, so-called point of no return, event in the transformation process, was analysed by inclusion of immortal HPV16E6E7 transduced derivatives (passage 30).

By this approach we identified PRDM14 and FAM19A4 as novel methylation targets in HPV-induced transformation, methylation of which became particularly evident in the immortal transductants, but in case of PRDM14 was also yet infrequently seen in early passage cells.

Methylation of the PRDM14 and FAM19A4 promoter region was verified by quantitative Methylation Specific PCR (qMSP) in an independent series of HPV-transfected keratinocyte cell lines. Primers and probe for qMSP are listed in Table 1. PRDM14 promoter methylation was detected in two HPV16 (FK16A, FK16B) and two HPV18 (FK18A, FK18B) immortalized keratinocyte cell lines. In addition high levels of PRDM14 methylation were detected in three hrHPV-positive cervical cancer cell lines (SiHa, HeLa and CaSki) as well as an HPV16 positive head and neck cancer cell line (93VU147T). Three isolates of HPV-negative primary keratinocytes (HFK) tested PRDM14 methylation negative (see Table 2).

Treatment of SiHa cervical cancer cells with the methylation inhibitor 5-aza-2 deoxycytidine (DAC) resulted in an upregulation of PRDM14 mRNA expression, indicating that PRDM14 promoter methylation regulates its gene expression in cervical cancer cells (FIG. 2).

Similar to PRDM14, FAM19A4 promoter methylation was detected in two HPV16 (FK16A, FK16B) and two HPV18 (FK18A, FK18B) immortalized keratinocyte cell lines as well as cervical (SiHa, HeLa and CaSki) and head and neck cancer (93VU147T) cell lines, the latter showing highest levels of FAM19A4 methylation. Three isolates of HPV-negative primary keratinocytes (HFK) tested FAM19A4 methylation negative (see Table 2).

Example 2

Functional Role of PRDM14 in Cervical Carcinogenesis

To determine the potential functional role of PRDM14 in cervical carcinogenesis, we transfected cells of the HPV16 containing cervical cancer cell lines SiHa and CaSki with a PRDM14 expression vector or an empty control vector (GFP). Ectopic PRDM14 expression in SiHa and CaSki PRDM14 transfectants was confirmed by RT-PCR. Following transfection cell apoptosis induction was measured by FACS analysis of cells stained for Annexin V and propidium iodide (PI). Compared to the empty vector control transfectants and untransfected parental cells, a strong induction of apoptosis was evident in PRDM14 overexpressing cells (FIG. 4). The strong induction of apoptosis upon ectopic expression of PRDM14 in cervical cancer cells is suggestive of a tumor suppressive role in cervical carcinogenesis. In analogy to the cervical cancer cell line results, ectopic expression of PRDM14 in the HPV16-positive head and neck cancer cell lines also resulted in the induction of apoptosis (FIG. 4). Hence these data suggest that PRDM14 has a tumor suppressive role in HPV-positive head- and neck cancers. Upon introduction of PRDM14 in Human Embryonic Kidney cells (HEK) no apoptosis induction was observed, indicating that the apoptosis induction observed in HPV-positive cancer cell lines does not result from a non-specific effect of the construct used for transfection.

Example 3

PRDM14 and FAM19A4 Promoter Methylation are Common Events in High Grade CIN Lesions, Cervical Squamous Cell Carcinomas, Adenosquamous Carcinomas, Adenocarcinomas and Neuroendocrine Carcinomas Next, we analysed PRDM14 and FAM19A4 promoter methylation in cervical tissue specimens by quantitative methylation specific PCR (qMSP) as described in Example 1. The housekeeping gene β-actin (ACTB) was chosen as a reference for total DNA input measurement. For all samples the quantity of measured methylated DNA was divided by the quantity of ACTB, and samples with ratios above a predefined cut-off (e.g. mean ratio normal controls (excluding major outliers)+2.58×standard deviation) were classified as positive.

We found that PRDM14 promoter methylation was detectable in 11% (2/18) of normal cervical control samples, 33% (13/40) of CIN1 lesions 55% (23/42) of CIN3 lesions and 100% (42/42) of cervical squamous cell carcinomas (SCC) (Table 3). The PRDM14 methylation levels detected at the different stages of disease are plotted in FIG. 5.

Next to cervical squamous cell carcinomas we also analysed PRDM14 promoter methylation in cervical adenocarcinomas. Adenocarcinomas, which constitute up to 20% of cervical carcinomas, are of particular interest as the incidence of cervical adenocarcinoma has remained the same or even increased in countries with a nation-wide cervical screening program. This indicates that cervical adenocarcinoma and its glandular precursor lesion, i.e. adenocarcinoma in situ (ACIS), are frequently missed by cytology based screening. Based on comparative genetic and epigenetic studies between cervical squamous cell carcinomas and cervical adenocarcinomas it has been found that both tumor histotypes develop via distinct carcinogenic pathways (Dong et al., 2001, Kang et al., 2005, Wilting et al., 2006, Henken et al., 2007). Consequently, most biomarkers enabling the detection of cervical squamous cell carcinoma do not necessarily detect cervical adenocarcinoma.

Methylation markers like CADM1, CDH1, DAPK1 and SOX17 are more specific for squamous cell carcinomas, whereas markers like RASSF1A, APC, DKK3 and SFRP2 are predominantly methylated in adenocarcinomas (Overmeer et al., 2008, Kang et al., 2005, Dong et al., 2001, van der Meide et al., 2011)

Figure 5:
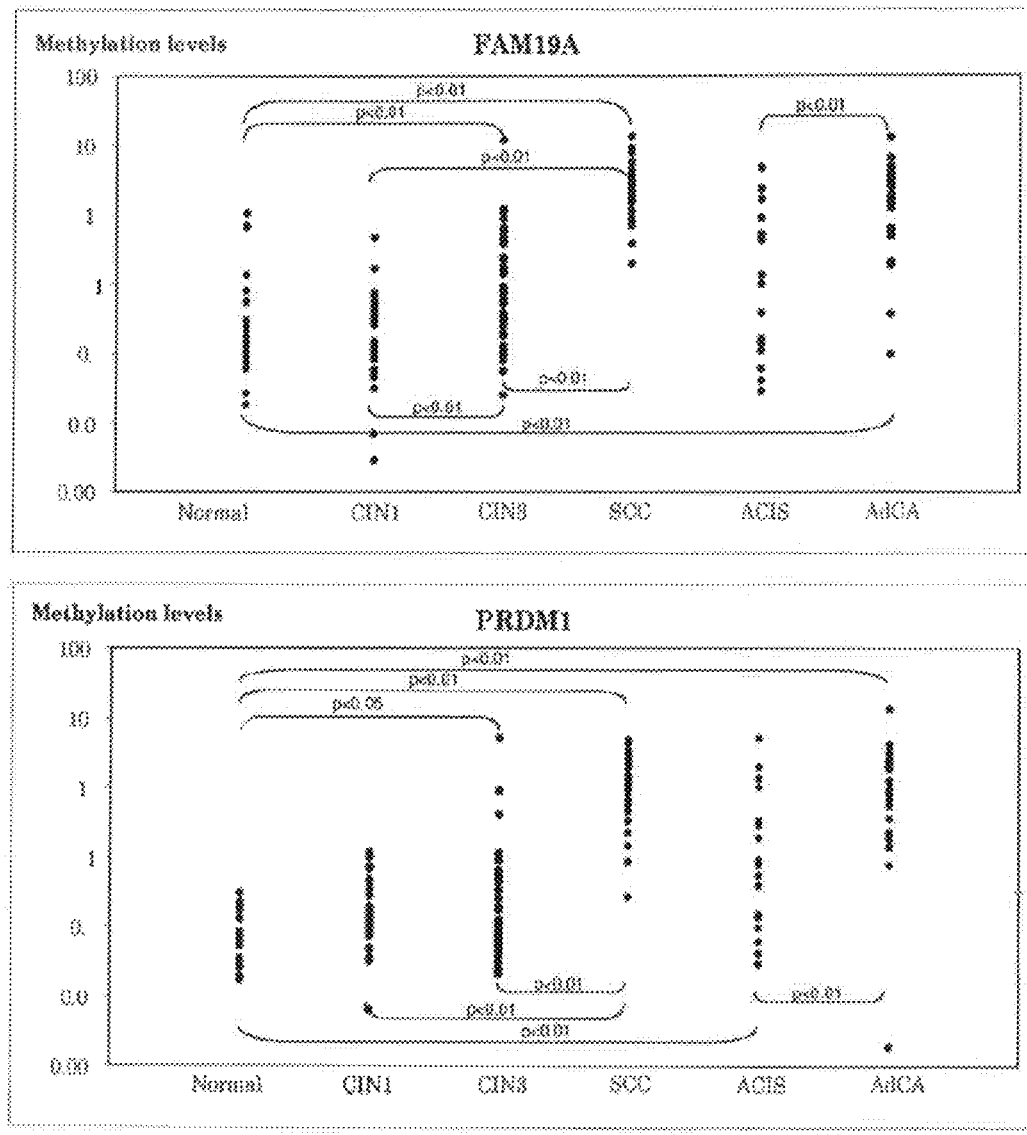
FIG. 5. Scatter plots of the levels of PRDM14 and FAM19A4 as measured by quantitative methylation specific PCR in cervical tissue specimens. On the y-axes levels of methylated DNA are presented; on the x-axes the samples are grouped for each disease stage and histotype. The level of methylation of PRDM14 and FAM19A4 increases with stage of disease and is detected in virtually all SCC and AdCA. Significant differences in methylation levels between disease categories are indicated.

Interestingly, PRDM14 promoter methylation appeared to be an exception as, in contrast to most known markers, it detected cervical adenocarcinomas at a similar frequency as squamous cell carcinomas; i.e. 97% (30/31) of adenocarcinomas showed PRDM14 promoter methylation and 57% (12/21) adenocarcinoma in situ tested PRDM14 methylation positive (FIG. 5, Table 3). Similar results have been obtained for cervical adenosquamous carcinomas and neuroendocrine carcinomas.

Therefore, PRDM14 promoter methylation appears to be a universal methylation marker for all cervical carcinoma histotypes.

Analysis of FAM19A4 promoter methylation revealed methylation positivity in in 19% (3/16) of normal cervical control samples, 12% (3/26) of CIN1 lesions, 43% (18/42) of CIN3 lesions and 100% (42/42) of cervical squamous cell carcinomas (SCC), 52% (11/21) of adenocarcinoma in situ (ACIS) and 92% (24/26) of adenocarcinomas (AdCA) (Table 3). The FAM19A4 methylation levels detected at the different stages of disease and histotypes are plotted in FIG. 5. Hence, FAM19A4 promoter methylation also represents a universal methylation marker for all cervical carcinoma histotypes

Example 4

Detection of PRDM14 and FAM19A4 Promoter Methylation in hrHPV-Positive Cervical Scrapes Using a case-control design of women participating in a population-based screening we studied cervical scrapes of hrHPV positive women in which ≥CIN 2 (including 2 carcinomas) was diagnosed (i.e., cases) versus hrHPV positive women in whom at maximum CIN 1 was diagnosed (i.e., controls). Cervical scrapes of these women were collected in preservation medium in which nucleic acids are well preserved.

PRDM14 methylation was detected in 23% (8/35) of hrHPV positive control women with normal cytology and 74% (17/23) of women with ≥CIN 2. FAM19A4 methylation was detected in 3% (1/35) of hrHPV positive control women with normal cytology and 52% (12/23) of women with ≥CIN 2. In a larger series of 200 consecutive hrHPV-positive cervical scrapes collected during the prospective population-based screening trial POBASCAM (Rijkaart et al., Lancet Oncology 2012) a subsequent validation analysis revealed that FAM19A detects >80% of women with ≥CIN3 at an assay threshold giving rise to a specificity of 50%. At a threshold corresponding to a specificity rate of 70%, 70% of women with ≥CIN3 are detected.

These data indicate that both PRDM14 and FAM19A4 methylation analysis enable the detection of underlying cervical disease (CIN2+) in hrHPV-positive cervical scrapes and thereby provide promising triage markers of cervical screening by primary HPV testing.

Example 5

FAM19A4 Methylation Analysis in Cervical Scrapes of Women with CIN3 Associated with a Short-Term and Long-Term HPV Infection In previous studies we compared CIN3 lesions of women with a short-term (<5 year) preceding HPV infection to CIN3 lesions of women with a long-term (5 year) preceding HPV infection with respect to DNA copy number alterations (Bierkens et al., Int J Cancer 2012: 131(4):E579-85). Duration of preceding hrHPV-infections served as a surrogate for lesion age according to which CIN3 lesion can be assigned a respectively lower and higher disease stage. The fact that significantly more DNA copy number alterations were detected in CIN3 lesions with a long-term preceding hrHPV infection, substantiates the assumption that this category represents a higher disease stage, so-called advanced CIN3 lesions, at increased cancer risk.

To determine whether FAM19A4 methylation analysis can detect these advanced CIN3 lesions, we analysed cervical scrapes of 19 women with CIN3 and a short term preceding hrHPV infection and 29 women with CIN3 and a long term HPV infection. Most interestingly, all (29/29; 100%) scrapes of women with advanced CIN3 lesions (long-term preceding hrHPV infection) were detected by FAM19A4 methylation, opposed to 42% (8/19) of scrapes of women with CIN3 lesions associated with a short-term hrHPV infection, so-called early CIN3 lesions. A methylation positive test result was based on assay thresholds settings giving rise to a 70% specificity. This remarkably high prevalence in women with advanced lesions suggests that testing for FAM19A4 methylation detects all women with advanced CIN3 lesions that need immediate referral for colposcopy.

Example 6

FAM19A4 Promoter Methylation in Cervical Scrapes of Cancer Patients

A total of 60 cervical scrapes of patients with cervical carcinomas where analysed for FAM19A4 methylation.

These included 10 adenocarcinomas, 2 adenocarcinomas in situ, 2 adenosquamous carcinomas, 43 squamous cell carcinomas and 3 undifferentiated carcinomas. All carcinomas, except 1 adenocarcinoma, tested positive for FAM19A4 methylation (specificity 70%). In addition to scrapes of cervical cancer patients, also a subset of scrapes of women with endometrial cancer was found to be positive for FAM19A4 methylation. Most interestingly, our complete series of cancer patient derived scrapes was found to test positive for a combination of FAM19A4 and hsa-miR124-2 methylation (Wilting et al., Mol Cancer 2010: 9, 167).

Hence, combined testing for FAM19A4 and hsa-miR124-2 methylation in cervical scrapes enables the detection of all (100%) cancers of both cervical and endometrial origin.

Example 7

PRDM14 and FAM19A4 Promoter Methylation in Self-Sampled Specimens

We subsequently analysed self-sampled cervico-vaginal specimens collected using either a VibaBrush (Rovers Medical Devices, Oss, the Netherlands) or a Delphi-screener (Delphi BioScience BV, Scherpenzeel, The Netherlands) during the course of a prospective study in which a total of 45,000 self-sampling packages were be sent to women who, even after a second reminder, did not respond to the invitation for regular cervical screening (See www.trialregister.nl, Trial no.NTR962 (PROHTECT trial)). Offering self-sampling for hrHPV-testing to non-attendees showed to re-attract up to 30% of these women to the screening programme (Gok et al., BMJ 2010; 340:c1040). Self-collected samples are equivalent to physician-taken ones with respect to HPV testing (Brink et al. J Clin Microbiol 2006; 44:2518-23). Testing for hrHPV in self-samples yields at least as much ≥CIN 2 lesions in this population as found by regular screening in a matched population of responder women (Bais et al., Int J Cancer: 2007, 120:1505-1510; Gok et al., BMJ 2010; 340:c1040). However, also for HPV self-sampling there is a need for triage tools to stratify hrHPV positive women into those with and without ≥CIN 2/3 and ≥adenocarcinoma in situ. Whereas conventional cytology cannot be reliably performed on self-collected cervico-vaginal specimens (Brink et al. J Clin Microbiol 2006; 44:2518-23), DNA methylation analysis can be applied to self-collected cervico-vaginal lavages (Eijsink et al., Gynecol Oncol 201E120:280-3.). Importantly, the present findings show that the methylation markers FAM19A4 and PRDM14 enable the detection of underlying CIN2+ not only when applied to self-collected cervico-vaginal lavage specimens but self-collected vaginal brush samples as well. The latter is a specimen type in which previous known markers often performed with low clinical sensitivity. Consequently, the PRDM14 and FAM19A4 markers can be considered as pan-detection markers performing equal on physician-taken cervical smears, lavage-based self-samples and brush-based self-samples.

A series of 177 self-collected vaginal brush samples of hrHPV positive women without evidence of clinically meaningful disease in follow-up (i.e. normal cytology/HPV- or CIN0/CIN1 histology) as well as 74 self-collected vaginal brush samples of hrHPV positive women with ≥CIN3 (68 CIN3, 4 SCC, 1 ACIS, 1 adenosquamous cell carcinoma proven within 36 months) were tested by qMSP for PRDM14 and FAM19A4 promoter methylation. FAM19A4 either or not combined with PRDM14 methylation analysis reached a sensitivity of 70% for ≥CIN3 at a specificity of 70%. Up to now, FAM19A4 methylation is surprisingly the only methylation marker that predicts on self-collected vaginal brush samples an underlying ≥CIN3 lesion in hrHPV-positive women with acceptable sensitivity (>60%). Much lower sensitivity rates were obtained on self-collected vaginal brush samples with other methylation markers or marker combinations. Since such a superior performance is not observed in conventional scrapes or cervico-vaginal lavage specimens, this finding is unexpected.

Additionally, a series of 350 self-collected cervico-vaginal lavage specimens of hrHPV positive women, including 272 hrHPV positive women without evidence of clinically meaningful disease in follow-up (i.e. normal cytology/HPV- or CIN0/CIN1 histology) as well as 78 cervico-vaginal lavage specimens of hrHPV positive women with ≥CIN3, was analysed for PRDM14 and FAM19A4 methylation. FAM19A4 either or not combined with PRDM14 methylation analysis revealed a sensitivity of 70% for ≥CIN3 at a specificity of 70%. This substantiates a pan-detection function of FAM19A4 either or not combined with PRDM14 methylation or other methylation markers on various sample types including cervical scrapings and self-collected (cervico)vaginal brush and lavage specimens.

In further studies we determined whether other methylation markers other than PRDM14 can be complementary to FAM19A4 for the detection of ≥CIN3 in self-collected vaginal brush and lavage samples. At specificity rates below 70% (60% and 50%) the methylation marker hsa-miR124-2 (Wilting et al. Mol. Cancer 2010: 9, 167) was found to be of additive value resulting in an increased sensitivity compared to testing for FAM19A4 alone.

These data show that PRDM14 and FAM19A4 promoter methylation analysis on self-sampled materials obtained from both self-collected vaginal brush samples and self-collected cervico-vaginal lavage specimens is well feasible and will improve the detection of underlying high-grade cervical disease. FAM19A4 in particular yields high sensitivity and specificity rates (70% versus 70%), exceeding those of other methylation markers or HPV16/18 genotyping, in both self-collected vaginal brush samples and self-collected cervico-vaginal lavage specimens. A combined analysis of FAM19A4 and hsa-mir124-2 was shown to be superior at the 50% and 60% specificity rates, compared to FAM19A4 alone.

Example 8

Figure 6:
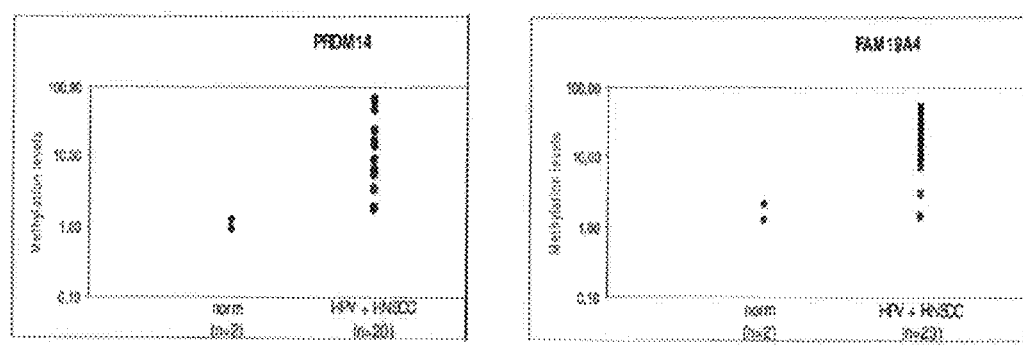
FIG. 6. PRDM14 and FAM19A4 methylation levels in hrHPV-positive head and neck tissue specimens (HNSCC: Head-and-Neck SCC). Methylation levels are significantly increased in carcinomas compared to controls.

PRDM14 and FAM19A4 Promoter Methylation Analysis in hrHPV-Positive Head and Neck Squamous Cell Carcinomas, Vulva Carcinomas and Precursor Lesions and Anus Carcinomas In order to determine whether promoter methylation of PRDM14 and FAM19A4 is also detectable in carcinomas other than cervical cancers associated with hrHPV, we analysed 20 hrHPV-positive head and neck (i.e. oropharyngeal) squamous cell carcinomas (HNSCC) and 2 normal oral mucosa samples by qMSP. Both PRDM14 and FAM19A4 methylation levels were significantly ($p<0.05$) increased in HNSCC compared to normal head and neck mucosa samples (FIG. 6). In fact in all (20/20) HNSCC PRDM14 methylation levels were increased compared to controls. In 90% (18/20) of HNSCC FAM19A4 methylation levels were increased compared to controls.

Additionally, we tested 3 hrHPV-positive vulva carcinomas, 4 precancerous vulva lesions (VIN3) and 3 hrHPV-positive anus carcinomas for PRDM14 and FAM19A4 methylation. All 11 lesions revealed high levels of PRDM14 methylation and all but 1VIN3 lesion showed high levels of FAM19A4 methylation, similar to cervical lesions.

These data indicate that non-cervical hrHPV-positive (pre)cancerous lesions, including those of the head- and neck region, vulva and anus, can be detected by FAM19A4 and/or PRDM14 methylation.

TABLE 1

Primer and probe sequences (5'-3') used for PRDM14 and FAM19A4 quantitative MSP analysis

| | Forward primer | Reverse primer | Probe |
|---|---|---|---|
| PRDM14 | TTATTAGCGGGTTAGACGTCGTTT (SEQ ID NO: 1) | CGTCCCGAAATCGAACCC (SEQ ID NO: 2) | CTTACTCTCCGCTCCCAATTCGAAAAATCC (SEQ ID NO: 5) |
| FAM19A4 | AGTCGGGCGGTTCGGTTA (SEQ ID NO: 3) | CCAAAAACGACGCGCAACTA (SEQ ID NO: 4) | CCCAACTAACGCGCTAA (SEQ ID NO: 6) |

TABLE 2

Summary of PRDM14 and FAM19A4 qMSP results on primary keratinocytes, HPV16 and HPV18-transfected keratinocytes (early and late passages of immortal FK16A, FK16B, FK18A and FK18B cells) and hrHPV positive cervical cancer cell lines

| | | PRDM14 qMSP | FAM19A4 qMSP |
|---|---|---|---|
| Primary keratinocytes | HFK1 | − | − |
| | HFK2 | − | − |
| | HFK3 | − | − |
| HPV16 and 18 immortalized keratinocytes | FK16A | + | + |
| | FK16B | + | + |
| | FK18A | + | + |
| | FK18B | + | + |
| Cervical cancer cell lines | SiHa | ++ | ++ |
| | HeLa | ++ | ++ |
| | CaSki | ++ | ++ |
| Head and neck cancer cell line | 93VU147T | ++ | ++ |

−: negative,
+: positive,
++: strongly positive

TABLE 3

Percentage of PRDM14 and FAM19A methylation positive cervical tissue specimens as determined by qMSP

| | PRDM14 | FAM19A4 |
|---|---|---|
| Normal | 11% (2/18) | 19% (3/16) |
| CIN1 | 33% (13/40) | 12% (3/26) |
| CIN3 | 55% (23/42) | 43% (18/42) |
| SCC | 100% (42/42) | 100% (42/42) |
| ACIS | 57% (12/21) | 52% (11/21) |
| AdCA | 97% (30/31) | 92% (24/26) |

CIN: cervical intraepithelial neoplasia
SCC: squamous cell carcinoma
ACIS: adenocarcinoma in situ
AdCA: adenocarcinoma

What is claimed is:

1. A method of identifying HPV-induced precursor lesions or HPV-induced invasive cancers comprising:
  a) obtaining a mammalian cell sample from a subject in need thereof;
  b) contacting said cell sample with a reagent, wherein said reagent detects FAM19A4 and wherein said reagent detects an alteration in the methylation of the FAM19A4 gene as compared to that of a comparable normal cell;
  c) identifying the presence of hypermethylation in the FAM19A4 gene in said cell, wherein a methylation specific PCR is performed, wherein said methylation specific PCR comprises bisulfite modification of DNA, followed by specific PCR reactions that target CpG rich sequences, wherein said specific PCR reactions comprise the primers of SEQ ID NO: 3, SEQ ID NO: 4, and the probe of SEQ ID NO: 6;
  d) identifying the presence of hypermethylation of hsa-miR 124-2 in said cell;
  e) indicating the sample has at least one of HPV-induced precursor lesions with invasive potential or HPV-induced invasive cancers when the presence of hypermethylation in the FAM19A4 gene in said cell and the presence of hypermethylation of hsa-miR 124-2 in said cell is identified.

2. The method of claim 1, wherein said HPV-induced high-grade precancerous lesion or HPV-induced invasive cancer is a high-grade premalignant cervical lesion or invasive cervical cancer.

3. The method of claim 1, wherein said HPV-induced invasive cancer is a high-risk HPV-induced invasive cancer.

4. The method of claim 1, wherein the reagent is a methylation sensitive restriction endonuclease, selected from the group consisting of BssHII, MspI, NotI and HpaII.

5. The method of claim 1, wherein said subject in need thereof is a subject having been tested positive for hrHPV.

6. A method of treating a subject selected as having HPV-induced precursor lesions or HPV-induced invasive cancers, comprising:
   a) obtaining a cell sample from said subject;
   b) contacting said cell sample with a reagent, wherein said reagent detects FAM19A4 and wherein said reagent detects an alteration in the methylation of the FAM19A4 gene as compared to that of a comparable normal cell;
   c) identifying the presence of hypermethylation in the FAM19A4 gene in said cell, wherein a methylation specific PCR is performed, wherein said methylation specific PCR comprises bisulfite modification of DNA, followed by specific PCR reactions that target CpG rich sequences, said specific PCR reactions comprise the primers of SEQ ID NO: 3, SEQ ID NO: 4, and the probe of SEQ ID NO: 6;
   d) identifying the presence of hypermethylation of hsa-miR 124-2 in said cell;
   e) indicating the sample has at least one of HPV-induced precursor lesions with invasive potential or HPV-induced invasive cancers when the presence of hypermethylation in the FAM19A4 gene in said cell and the presence of hypermethylation of hsa-miR 124-2 in said cell is identified; and
   f) initiating treatment of said subject.

* * * * *